United States Patent [19]
Vaillancourt et al.

[11] Patent Number: 5,472,430
[45] Date of Patent: Dec. 5, 1995

[54] PROTECTED NEEDLE ASSEMBLY

[75] Inventors: Vincent L. Vaillancourt, Livingston; John J. Welter, Ocean, both of N.J.

[73] Assignee: VLV Associates, East Hanover, N.J.

[21] Appl. No.: 108,994

[22] Filed: Aug. 18, 1993

[51] Int. Cl.$^6$ .............................. A61M 5/32; A61B 5/00; B65D 81/00
[52] U.S. Cl. ............................................ 604/198; 128/763
[58] Field of Search .................................. 128/763, 764; 604/110, 165, 170, 197, 198, 263, 264

[56] References Cited

U.S. PATENT DOCUMENTS

| | | | |
|---|---|---|---|
| 3,134,380 | 5/1964 | Armao | 604/198 |
| 3,354,881 | 11/1967 | Bloch | 604/198 |
| 4,775,369 | 10/1988 | Schwartz | 604/198 |
| 4,892,107 | 1/1990 | Haber | 604/198 |
| 4,894,055 | 1/1990 | Sudnak | 604/263 |
| 4,911,693 | 3/1990 | Paris | 604/198 |
| 4,923,447 | 5/1990 | Morgan | 604/198 |
| 4,932,940 | 6/1990 | Walker et al. | 604/198 |
| 5,015,242 | 5/1991 | Heifetz | 604/198 |
| 5,088,986 | 2/1992 | Nusbaum | 604/198 |
| 5,104,382 | 4/1992 | Brinkerhoff et al. | 604/165 |
| 5,106,379 | 4/1992 | Leap | 604/198 |
| 5,209,739 | 5/1993 | Talalay | 604/198 |
| 5,242,401 | 9/1993 | Colsky | 604/198 |
| 5,292,314 | 3/1994 | D'Alessio et al. | 604/198 |

Primary Examiner—C. Fred Rosenbaum
Assistant Examiner—Frank Wilkens, III
Attorney, Agent, or Firm—McAulay Fisher Nissen Goldberg & Kiel

[57] ABSTRACT

The protected needle assembly employs a retractable sheath which can be moved from an extended protected position over a hollow needle to a retracted position exposing the hollow needle. A projection carried on the sheath is disposed in a guide slot having a circumferentially directed portion for receiving the projection. In addition, a spring or resilient sleeve is provided between the movable sheath and the housing to not only bias the sheath longitudinally of the hollow needle but also in a circumferential manner. In order to release the sheath, the needle assembly is brought into contact with a patient's skin or a septum and twisted. Thereafter, an axial force on the needle assembly causes the sheath to be retracted while the hollow needle penetrates through the skin or septum. Other embodiments are provided wherein a blunt needle can be moved within a hollow needle from an extended position protecting the hollow needle and a retracted position permitting exposure of the hollow needle.

27 Claims, 3 Drawing Sheets

PROTECTED NEEDLE ASSEMBLY

This invention relates to a protected needle assembly. More particularly, this invention relates to a needle assembly constructed in a manner to prevent needle sticks.

As is known, one major problem with a hypodermic needle as well as other needles is the threat of cutting oneself or another thereby exposing a blood vessel to the environment. This has become especially important in a hospital atmosphere where AIDS patients or AIDS members of a staff can infect others by having their blood interact, for example, by touching another person.

Various techniques have been proposed to overcome this problem. For example, in some cases, use has been made of a shield of cap which is placed over a needle after use. Generally, this is intended to allow only a one-time use of the needle with an automatic covering system which prevents further use. However, during actual use of such a needle, the needle does not remain totally protected. Further, if the needle is re-used, there is no provision to sheath the needle.

U.S. Pat. No. 4,629,453 describes a protection device for a hypodermic needle which uses a protective cap which can be fitted over a needle when the needle is not in use.

U.S. Pat. No. 4,735,618 describes a protective enclosure for hypodermic needles which employs a cap-like needle guard which is positioned about a free end of a needle while being connected via collapsible arms to a tubular sleeve mounted about a needle housing. When in use, the cap is pressed against a patient under a sufficient force to cause collapsing of the collapsible arms so that the cap slides back over the needle. However, when not intended for use, any accidental pushing in on the cap by a user can cause an inadvertent needle stick.

U.S. Pat. No. 3,134,380 describes a shielded hypodermic needle wherein a needle is sheathed within a collapsible tube so that upon collapsing of the tube, the needle is exposed. In addition, a spring is provided within the tube so as to return the collapsed tube to an extended state.

U.S. Pat. No. 4,725,267 describes the use of a resilient collapsible sheath which can be mounted over a needle to contain the needle when not in use.

U.S. Pat. No. 4,695,274 describes a removable needle attachment consisting of a needle-holding member and a safety jacket. As described, the jacket is provided with a slot which receives a guide tab of the needle-holding member so as to prevent sliding of the safety jacket back and forth on the needle holding member in order to permit piercing of the needle through a wall of the safety jacket. However, in such a construction, as in other similar constructions, a risk of inadvertent needle sticking occurs should the guide tab be disposed in an unlocking condition within the slot.

Accordingly, it is an object of the invention to provide a protective cover for shielding a hypodermic needle which is relatively fool proof.

It is another object of the invention to provide a needle assembly with a protective sheath which is retained in place until actual use is made of the needle of the assembly.

It is another object of the invention to prevent inadvertent passage of a needle from a protected state within a protective sheath.

Briefly, the invention provides a protected needle assembly which is comprised of a housing, a needle mounted on the housing for percutaneous insertion into a patient and a sheath disposed about the needle with one end extending beyond the needle in protective relation. The sheath is also movable longitudinally of the needle between an extended position covering over the needle and a retracted position exposing the needle.

In accordance with the invention, at least one projection is provided on the sheath and a locking means is mounted on the housing for releasably locking the sheath in the extended position via the projection. This locking means includes a guide slot receiving the projection of the sheath. Further, the guide slot has a circumferentially directed portion for receiving the projection in the extended position of the sheath and a longitudinally directed portion for receiving the projection during movement of the sheath to the retracted position.

Further, in accordance with the invention, a resilient means is provided for biasing the projection into the circumferentially directed portion of the guide slot.

The locking means and the resilient means cooperate in the assembly so as to provide a substantially fool-proof locking arrangement whereby the needle does not become unsheathed until actual use. That is, the sheath is always maintained in the extended position to protect the needle except when the sheath is pressed against the skin, septum or closure which must be pierced to obtain or dispense a medicament or other fluid. At the time the practitioner wishes to unsheath the needle for piercing purposes, a simple twist motion while some pressure is applied to the skin, septum or other closure activates the locking means such that the needle can now be operative. After use and as the needle is being withdrawn, the sheath automatically returns to the extended or "guard" position under the bias of the resilient means. For example, in order to use the needle, the sheath is brought into contact with the skin. A slight twist is then imparted to the housing such that the sheath remains fixed relative to the skin while the housing rotates. The projection on the sheath is thus moved from the circumferentially directed portion of the guide slot into the longitudinally directed portion thereby allowing continued pressure on the housing to cause the needle to pass through the sheath into the patient. Upon removal of the needle and sheath, the sheath springs back into the extended position over the needle and the force which has been introduced into the resilient means biases the projection on the sheath back into the circumferentially directed portion of the guide slot to lock the sheath in the extended position.

In one embodiment, the locking means is in the form of a sleeve which is mounted at one end on the housing and which receives the sheath therein in telescopic relation. In this embodiment, the resilient means may be in the form of a rubber sleeve which is secured to the housing at one end and secured to the sheath at an opposite end. The sheath may also be hollow at both ends or may be provided with a sealing membrane at the distal end through which the needle may pass when put into use.

In another embodiment, the resilient means is in the form of a coiled spring which is disposed between the housing and the sheath and which is secured thereto so as to permit twisting of the spring whereby the projection on the sheath is biased into the circumferentially directed portion of the guide slot.

In any of these embodiments, the projection may extend beyond the guide slot in order to permit manual operation thereof.

In still another embodiment, the protected needle assembly may employ a housing, a hollow needle mounted on the housing and a blunt needle concentrically within the hollow needle for movement between an extended position with one end projecting out of the hollow needle and a retracted position with the end within the hollow needle. In this embodiment, at least one projection is provided on the blunt needle and a locking means is provided on the housing for releasably locking the blunt needle in the extended position. As above, this locking means includes a guide slot in the housing receiving the projection. Also, as above, the guide slot has a circumferentially directed portion receiving the projection in the extended position of the blunt needle and a longitudinally directed portion receiving the projection during movement of the blunt needle to the retracted position.

The assembly also includes a resilient means for biasing the projection into the circumferentially directed portion of the guide slot. For example, the resilient means may be in the form of a rubber sleeve which is secured between the blunt needle and the hollow needle.

This assembly may also be provided with a vacuum holder needle which extends coaxially of the blunt needle for effecting a blood transfer therebetween. In this case, the housing has a cup-shaped portion extending concentrically of the vacuum holder needle as well as a rubber sheath mounted on the housing to enclose the vacuum holder needle.

In still another embodiment, the blunt needle may be of solid construction, example for, for use as an epidural needle.

In still another embodiment, a blood collecting assembly can be provided with a protected needle. For example, the blood collecting assembly includes a housing, a blunt needle slidably mounted in the housing for movement between an extended position and a retracted position as well as a hollow needle mounted concentrically about the blunt needle. In accordance with the invention, a sleeve or ring is rotatably mounted on the housing at one end thereof and secured to the hollow needle at the opposite end. Further, the sleeve is provided with a guide slot having a pair of circumferentially directed portions and a longitudinally directed portion therebetween.

In this embodiment, a projection is secured to the blunt needle within the sleeve and is received in the guide slot for movement from one of the circumferentially directed portions to secure the blunt needle in the extended position while projecting from the hollow needle to the other of the circumferentially directed portions to secure the blunt needle in the retracted position while disposed within the hollow needle.

A resilient means is also provided for biasing the projection into a respective one of the circumferentially directed portions of the guide slot to maintain the blunt needle in the respective positions thereof. For example, the resilient means may be in the form of a spring which abuts the sleeve at one end and which is secured to the projection at the opposite end to permit resilient rotation of the sleeve.

The invention also provides a method for protecting a hollow needle. In this respect, a sheath is disposed in telescopic relation relative to a hollow needle having a sharp end for movement between an extended position projecting beyond the needle and a retracted position within the plane of the needle. In accordance with the invention, the sheath is locked in the extended position against movement under a longitudinally applied force on the sheath.

In order to unlock the sheath for movement from the extended position to the retracted position, the sheath is rotated relative to the needle and thereafter a longitudinally directed force is applied on the sheath to move the sheath from the extended position to the retracted position.

The rotation of the sheath as well as the movement of the sheath from the extended position to the retracted position is made against a resilient force restoring means. The sheath is thus biased back to the extended and locked position under the force imparted to the resilient means.

The operation of this embodiment differs from the above and noted embodiments in that the blunt needle, for example a blunt ended cannula, protrudes beyond the hollow needle. When the user is ready to penetrate the skin, the user turns the rotatable sleeve, for example, clockwise until the projection leaves the circumferentially directed portion of the guide slot and enters the longitudinally disposed portion. Once the projection reaches this longitudinally disposed portion, a gentle penetrating pressure causes the blunt needle to recess while the hollow needle is now free to penetrate the skin and behave in a normal fashion. As pressure is applied, the projection rides along the longitudinally disposed slot until reaching the second circumferentially disposed portion of the slot. At this time, the projection moves into the second circumferentially directed portion of the slot due to the residual twisting moment of the spring. As a result, the projection maintains the blunt needle in the retracted position so that the hollow needle is continually armed (normal operating condition).

When the hollow needle is to be withdrawn from the patient or vessel, the sleeve is again turned clockwise so that the projection is moved back to the longitudinally disposed portion of the guide slot. This, in turn, allows the blunt needle to again exit the hollow needle into the extended position under the resilient biasing force of the spring thereby protecting the sharpened end of the hollow needle. When the blunt needle reaches the extended position, the projection will spring back into the first circumferentially disposed portion to look the blunt needle in place.

In the alternative, the projection and guide slot may be disposed in a reversed fashion. For example, the guide slot may be disposed in the movable sheath while the projection is formed on the housing disposed concentrically about the movable sheath.

The invention also provides a method for protecting a hollow needle. In this respect, a sheath is disposed in telescopic relation relative to a hollow needle having a sharp end for movement between an extended position projecting beyond the needle and a retracted position within the plane of the needle. In accordance with the invention, the sheath is locked in the extended position against movement under a longitudinally applied force on the sheath.

In order to unlock the sheath for movement from the extended position to the retracted position, the sheath is rotated relative to the needle and thereafter a longitudinally directed force is applied on the sheath to move the sheath from the extended position to the retracted position.

The rotation of the sheath as well as the movement of the sheath from the extended position to the retracted position is made against a resilient force restoring means. The sheath is thus biased back to the extended and locked position under the force imparted to the resilient means.

These and other objects and advantages will become more apparent from the following detailed description taken in conjunction with accompanying drawings wherein.

Figure 1:
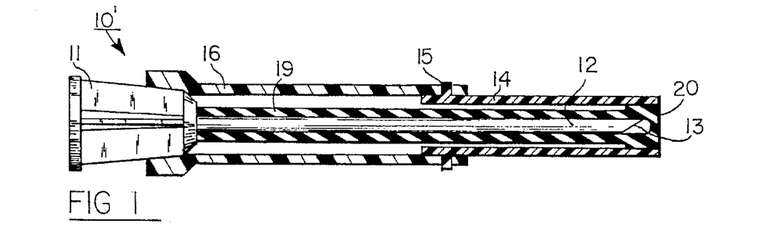
FIG. 1 illustrates a cross-sectional view of a protected needle assembly constructed in accordance with the invention.

Referring to FIG. 1, the protected needle assembly 10 comprises a housing 11, a needle 12 having a sharp end 13 mounted on the housing 11 for percutaneous insertion into a patient as well as a sheath 14 which is disposed concentrically about the needle 12 with one end extending beyond the needle 12 in protective relation. In addition, the sheath 14 which may be of a rigid plastic material has at least one projection 15 which extends radially of the sheath 14.

Figure 4:
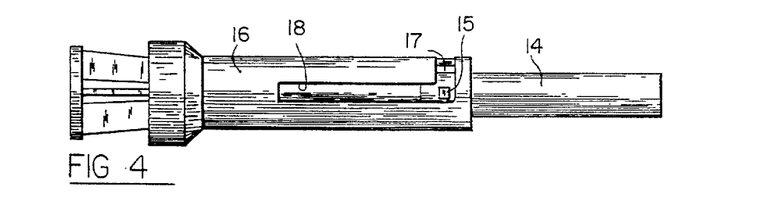
FIG. 4 illustrates a plan view of the assembly of FIG. 1.

The assembly 10 also includes a locking means 16 in the form of a rigid tube which is mounted on the housing 11 for releasably locking the sheath 14 in the extended position. As indicated in FIG. 4, the tube 16 has a guide slot which receives the projection 15 of the sheath 14. This slot includes a circumferentially directed portion 17 which receives the projection 15 in the extended position of the sheath 14 as well as a longitudinally directed portion 18 for receiving the projection 15 during movement of the sheath from the extended position to a retracted position (not shown). In this respect, the sheath 14 is movable longitudinally of the needle 12 between the extended position shown in FIGS. 1 and 4 covering over the needle 12 and a retracted position (not shown) exposing the needle 12.

Referring to FIG. 1, the assembly 10 also includes a resilient means in the form of a rubber sleeve 19 for biasing the projection 15 into the circumferentially directed portion 17 of the guide slot. As shown, the rubber sleeve 19 is secured to the housing 11 at one end and is secured to and within the sheath 14 at the opposite end. Any suitable means may be used to effect securement of the rubber sleeve 19 to the housing 11 and the sheath 14. As also shown in FIG. 1, the rubber sleeve 19 has a wall 20 at the distal end in facing relation to the sharp needle end 13 for piercing thereby. The rubber sleeve 19 thus serves to completely enclose the needle 12 so as to maintain the needle 12 in a sterile condition.

When the projection 15 on the sheath 14 is within the circumferential portion 17 of the slot of the tube 16, the sheath 14 cannot be moved from the extended position shown in FIG. 1. Thus, in order to use the needle assembly 10, the face of the wall 20 of the rubber sleeve 19 is brought against the skin of a patient or other suitable septum. At this time, the housing 11 is rotated slightly for example, in a counter-clockwise direction as viewed in FIG. 4 so as to move the tube 16 in the same direction and thus align the projection 15 on the sheath 14 with the longitudinally disposed portion 18 of the guide slot (see FIG. 4). Continued pressure against the sheath 14 via the housing 11 causes the tube 16 to slide telescopically along the sheath 14 with the projection 15 sliding within the longitudinally disposed portion 18 of the guide slot. At the same time, the needle 12 pierces through the wall 20 of the rubber sleeve 19 into the patient or through the septum, as the case may be. During this time, the rubber sleeve 19 is twisted between the wall 20 which is against the skin or septum and the end which is secured to the housing 11. This twisting imparts a residual stress in the rubber sleeve 19 so that when the needle 12 is pulled from the patient or septum, the sleeve 19 not only springs back into the extended position shown in FIG. 1 causing the sheath 14 to move to the extended position, but also imparts a slight turn on the sheath 14 so as to again place the projection 15 in the circumferentially directed portion 17 of the guide slot in the tube 16. This automatically effects a re-locking of the sheath in the extended position.

During movement of the needle 12 through the wall 20, the rubber sleeve 19 collapses in accordion-type manner thereby imparting a restoring force to the rubber sleeve 19 to bias the sleeve 19 and, thus, the sheath 14 into the extended position shown in FIG. 1 when the needle 12 is retracted from the patient or a septum.

The rubber sleeve 19 together with the locking means afforded by the projection 15 of the sheath 14 and the guide slot of the rigid tube 16 brings about a fool-proof assembly whereby the needle 12 cannot be exposed unless there is an intentional twisting force imposed upon the distal end of the rubber sleeve 19. Thus, inadvertent needle sticks due to a simple pressing of the needle assembly against a surface can be avoided.

Figure 2:
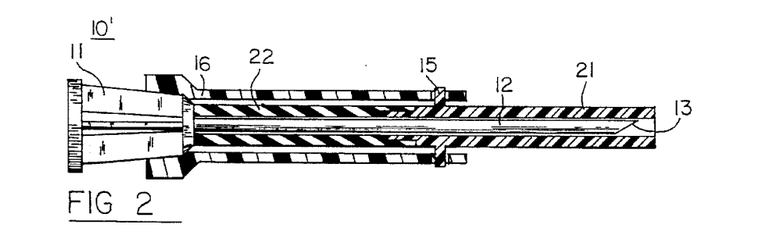
FIG. 2 illustrates a modified protected needle assembly employing a rubber sleeve as a resilient member in accordance with the invention.

Referring to FIG. 2, wherein like reference characters indicate like parts as above, the needle assembly 10' can be constructed in a modified manner. In this case, a sheath 21 in the form of a hollow transparent tube is placed about the needle 12 in order to move between the extended position shown in FIG. 2 and a retracted position (not shown) exposing the needle 12. As above, the sheath 21 is provided with a projection 15 which fits into a guide slot of a rigid tube 16 in a manner as indicated in FIG. 4.

In addition, a resilient means in the form of a rubber sleeve 22 is secured to the housing 11 at one end while being secured to the sheath 21 at the opposite end in a manner such that the sleeve 22 and sheath 21 are coaxially disposed about the needle 12.

In this embodiment, the needle assembly 10' operates in a similar fashion as the embodiment of FIG. 1.

Figure 3:
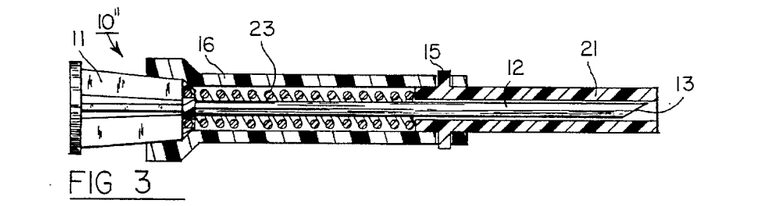
FIG. 3 illustrates a cross-sectional view of another embodiment employing a coil spring in accordance with the invention.

Referring to FIG. 3, wherein like reference characters indicate like parts as above, the protected needle assembly 10" may employ a spring 23 as the resilient means for biasing the projection 15 on a sheath 21 into the circumferentially directed portion of the guide slot. This spring 23, as the rubber sleeves 19, 22 described above, not only provides a restoring force to move the sheath 21 from the retracted position (not shown) to the extended position shown in FIG. 3 but also has a residual twisting force which biases the projection 15 of the sheath 21 into the circumferentially directed portion 17 of the guide slot of the rigid tube 16.

The spring 23 is secured at one end to the sheath 21 in a suitable manner while being secured at the opposite end to either the housing 11 or the tube 16 in a suitable manner so as to permit twisting of the spring 23 when there is a relative rotation between the sheath 21 and the housing 16.

Figure 5:
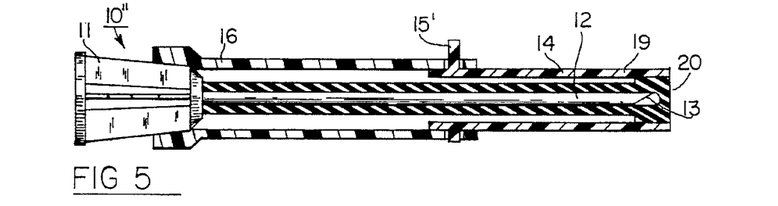
FIG. 5 illustrates a view similar to FIG. 1 employing a radially projecting projection in a locking means in accordance with the invention.

Referring to FIG. 5 wherein like reference characters indicate like parts as above, the projection 15' on the sheath 14 may extend radially beyond the rigid tube 16 so as to permit manual actuation thereof.

In the embodiment of FIGS. 2 and 3, the sheath 21 may be made of a transparent material in order to permit viewing of the needle 12 and, particularly, the sharp cutting end 13.

Figure 6:
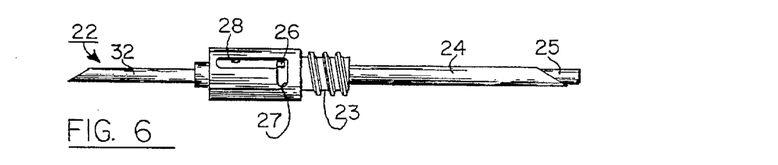
FIG. 6 illustrates a schematic view of a modified protected needle assembly in accordance with the invention employing a blunt needle.

Referring to FIG. 6, the protected needle assembly 24 may also be incorporated in other than a hypodermic type needle. For example, the needle assembly 24 may have a housing 25, a hollow needle 26 fixedly mounted on the housing 25 and extending therefrom, and a blunt needle 27, for example, a blunt ended cannula, concentrically within the hollow needle 26 for movement between an extended position as shown with one end projecting out of the hollow needle 26 and a retracted position (not shown) with the end within the hollow needle 26. As indicated in FIG. 6, the blunt needle 27 is provided with at least one projection 28 within the housing 25. In addition, a locking means is provided on the housing 25 for releasably locking the blunt needle 27 in the extended position. This locking means includes a guide slot in the housing 25 for receiving the projection 28 as indicated in FIG. 6. The guide slot, as above, has a circumferentially directed portion 29 receiving the projection 28 in the extended position of the blunt needle 27 and a longitudinally directed portion 30 for receiving the projection 28 during movement of the blunt needle 27 to a retracted position.

The assembly 24 also has a vacuum tube needle 31 extending coaxially from the blunt needle 27 for the transfer of blood or other fluid therebetween.

As above, the housing 25 may contain a resilient means in the form of a spring such as in FIG. 3 for biasing the blunt needle 27 to the extended position, i.e., to the right as viewed. At the same time, the spring biases the projection 28 on the blunt needle 27 to a position within the circumferentially directed portion 29 of the guide slot.

Figure 7:
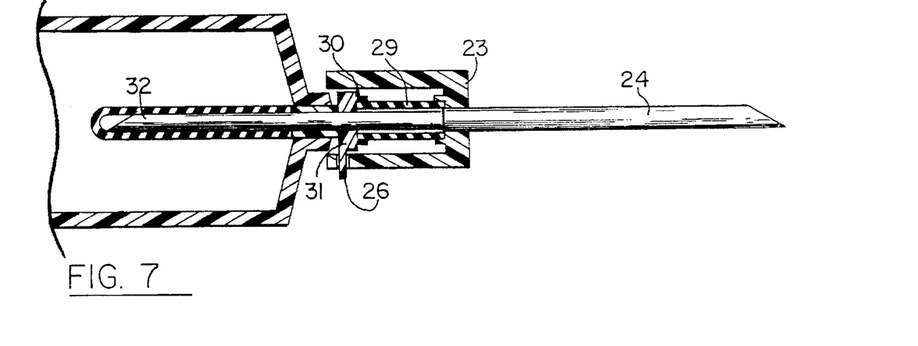
FIG. 7 illustrates a detailed view of a further modified needle assembly employing a blunt needle in accordance with the invention.

Referring to FIG. 7 wherein like reference characters indicate like parts as above, the needle assembly 32 may be constructed with a hollow needle 26 which is to be rotated relative to a non-rotatable blunt needle 27. In this case, the hollow needle 26 extends from a housing 25 while the blunt needle 27 is slidably mounted within the hollow needle 26. As above, the housing 25 has a guide slot, as above, formed therein while the blunt needle 25 carries a collar 33 on which a projection 34 is disposed for sliding within the guide slot. As indicated, the collar 33 also serves as a support for receiving a mounting tube 34' to which a rubber sleeve 35 is secured. The opposite end of the rubber sleeve 35 is secured to the housing 25 via suitable means such as an adhesive or by being fixedly secured between the housing 25 and hollow needle 26.

As indicated, the mounting of the rubber sleeve 35 is such that the sleeve 35 is stretched into the position illustrated when the blunt needle 27 is moved into the retracted position, i.e. to the left, as viewed, so as to impart a bias in the sleeve 35 to return the blunt needle 27 to the extended position (not shown).

As above, when the housing 25 is rotated relative to the blunt needle 27, the projection 34 moves out of the circumferentially directed portion of the guide slot into the longitudinally directed portion of the guide slot. At the same time, the rubber sleeve 35 has a twist imparted thereto which serves to bias the projection 34 back into the circumferentially directed portion of the guide slot.

In use, the blunt needle 27 can be brought up against a septum or the like. Thereafter, a slight turning action is imparted to the housing 25 so as to rotate the housing 25 relative to the projection 34 and blunt needle 27 thereby unlocking the blunt needle 27. Continued pressure on the housing 25 in a coaxial direction causes the blunt needle 27 to retract within the hollow needle 26 while the hollow needle 26 is pushed through the skin of a patient or into a septum. Upon withdrawal of the hollow needle 26, the blunt needle 27 is caused to return to the extended position via the restoring force in the rubber sleeve 35. At the same time, the twisted sleeve 35 returns to the unstressed state so as to again move the projection 34 into the circumferentially directed portion of the guide slot thereby locking the blunt needle 27 in the extended state.

Figure 8:
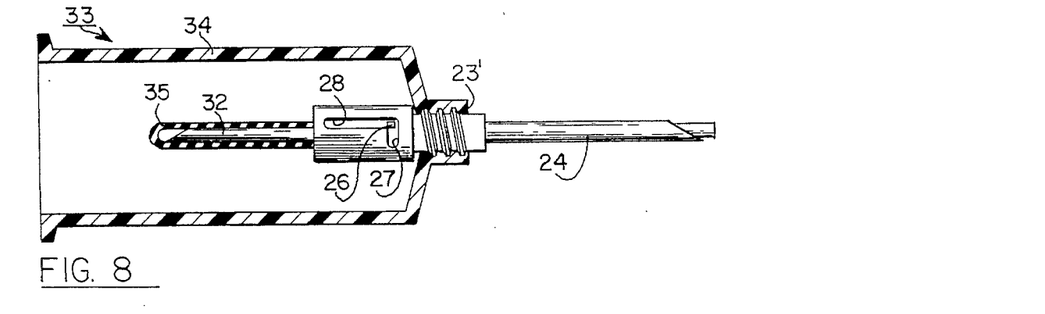
FIG. 8 illustrates a view of the assembly of FIG. 6 used as a blood collecting assembly.

Referring to FIG. 8, wherein like reference characters indicate like parts as above, the needle assembly 36 may be constructed so that the housing 25 has a cup-shaped portion 37 extending concentrically about the vacuum tube needle 31 so that this needle 31 is retained in a recessed condition. As indicated, the cup-shaped portion 37 is threaded onto the housing 25 via a thread. In addition, a rubber sheath or cap 28 is mounted on the housing 25 to enclose the vacuum tube needle 31. Such an assembly can be used for blood collection as is known.

Figure 9:
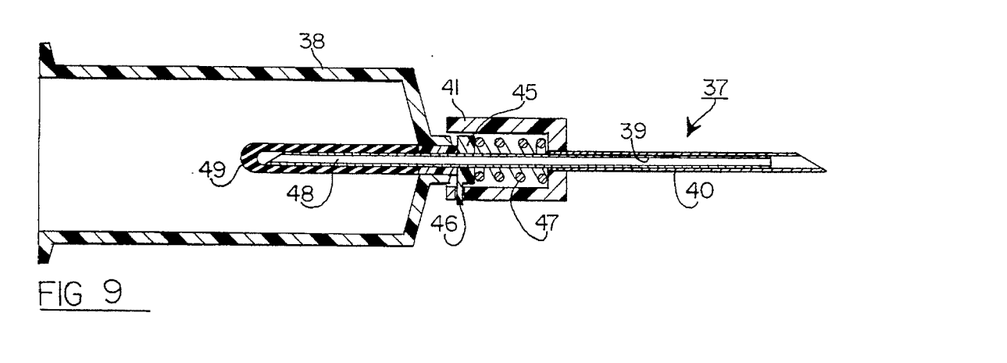
FIG. 9 illustrates a blood collecting assembly constructed in accordance with the invention.
Figure 10:
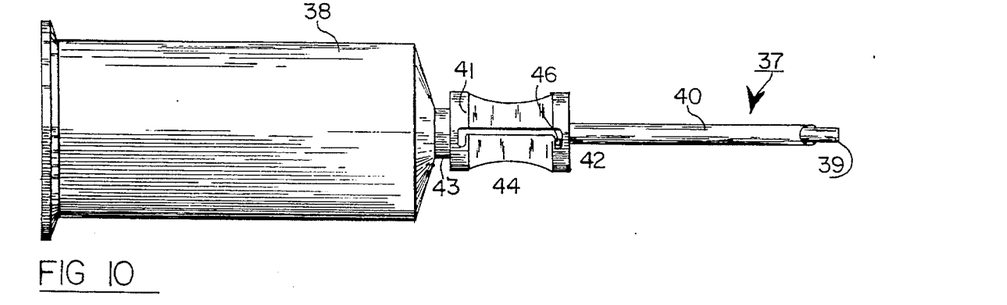
FIG. 10 illustrates an epidural needle constructed in accordance with the invention.

Referring to FIGS. 9 and 10, a blood collecting assembly 39 may also be constructed to incorporate features as above. As indicated above, the blood collecting assembly 39 comprises a housing 40, a blunt needle 27 slidably mounted in the housing 40 for movement between an extended position as shown in FIG. 10 and a retracted position as shown in FIG. 9. In addition, a hollow needle 26 is mounted concentrically about the blunt needle 27. This hollow needle 26 extends into a sleeve 41 which is rotatably mounted on the housing 40 at one end and secured to the hollow needle 26 at the opposite end. As indicated in FIG. 9, the sleeve 41 has a guide slot therein including a pair of circumferentially directed portions 42, 43 and a longitudinally directed portion 44 therebetween. The sleeve 41 may be in the form of a plastic ring and may be shaped so as to provide a finger hold as indicated in FIG. 10.

A locking means is also secured to the blunt needle 27 within the sleeve 41. As indicated in FIG. 9, this locking means includes a block 45 which is fixedly mounted on the blunt needle 39 in any suitable fashion and a projection 46 which extends from the block 27 into the guide slot. A resilient means in the form of a coiled spring 47 is also disposed within the sleeve 41 for resiliently biasing the projection 46 into the one or the other of the circumferentially directed portions 42, 43 of the guide slot to maintain the blunt needle 27 in either the extended position or the retracted position thereof. As indicated, the spring 47 is secured to the sleeve 41 at one end and is secured to the block 45 on which the projection 46 is mounted at the opposite end in order to permit resilient rotation of the sleeve 41 relative to the block 45.

As shown in FIG. 9, the blunt needle 27 terminates within the housing 40 in a vacuum tube needle 48 while a rubber sheath 49 is mounted within the housing 40 to enclose the vacuum tube needle 48. As is also indicated in FIG. 9, the vacuum tube needle 48 and sheath 49 are recessed within the housing 40.

In use, the blunt needle 27 is brought against a septum or patient's skin in the condition shown in FIG. 10. At this time, the sleeve 41 is manually grasped and rotated, for example, in a clockwise manner so as to move the projection 46 out of the distal circumferentially disposed portion 42 of the guide slot into the longitudinally disposed portion 44 of the guide slot. Continued force on the housing 40 to the left causes the blunt needle 27 to retract within the hollow needle 26 against the force of the spring 47 within the sleeve 41. Thereafter, when the projection 46 is located at the remote circumferentially directed portion 43 of the guide slot (see FIG. 9), the twisted spring 47 untwists to bias the projection 46 into the circumferentially directed slot 43 thereby locking the blunt needle 27 in the retracted position relative to the hollow needle 26. A reverse operation is carried out when the hollow needle 26 is to be retracted from the patient or septum.

Figure 11:
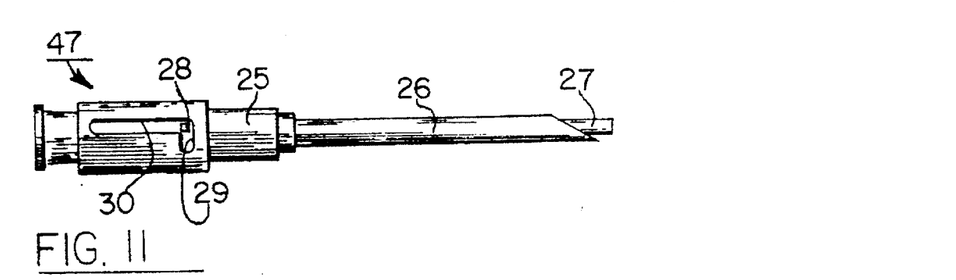
FIG. 11 illustrates a plan view of a guide slot of modified construction in accordance with the invention.

While the blunt needle 27 has been described as being a cannula, the blunt needle may also be of solid construction for use in an epidural needle 47 as indicated in FIG. 11.

Figure 12:
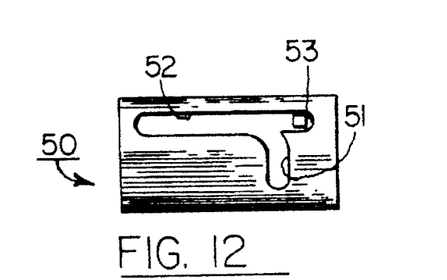
FIG. 12 illustrates a plan view of the a modified guide slot in accordance with the invention.

Referring to FIG. 12, the guide slot 50 may be modified from that as described above. As indicated, the guide slot includes a circumferentially directed portion 51 and a longitudinally directed portion 52. In addition, the guide slot 50 has a third portion 53 which extends from the longitudinally directed portion 52 somewhat beyond the circumferentially directed portion 51. Thus, when a projection is moving to the right, as viewed, within the longitudinally disposed portion 52, the projection is influenced to first move into the extended portion 53. That is, when the pressure is released, the projection (not shown) will move to the right along the longitudinally disposed portion 52 under the restoring force of a spring (not shown) into the extended portion 53. This allows the sheathed needle (not shown) to again be exposed should a longitudinally applied force be again imposed upon the sheath. On the other hand, as an unsheathing force is imposed, the projection slides rearwardly, as viewed, so as to move opposite the circumferentially directed portion 51. The twisted spring then restores the projection into the circumferentially directed portion 51 in a secure manner to lock the sheath in place and, thus, prevent unsheathing of the needle.

Figure 13:
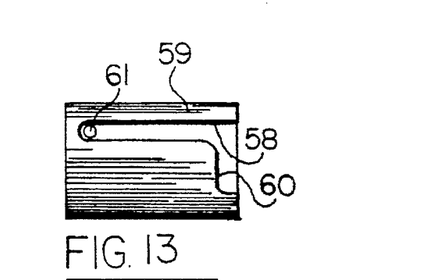
FIG. 13 illustrates a plan view of a modified open ended guide slot in accordance with the invention.

Referring to FIG. 13, the guide slot in any of the above embodiments may be modified so as to be open ended. In this respect, the guide slot has a longitudinally directed portion 58 which extends to an end of the housing 59 in which the guide slot is disposed. In addition, a circumferentially directed portion 60 is disposed at the end of the housing 58 to accommodate a projection 61 on a sheath (as in FIGS. 2 and 3) or otherwise as described above. In this respect, the guide slot functions as a cam relative to the projection 61.

The invention thus provides a needle assembly which requires a conscious effort on the part of the user to impose a twisting action on the forward end of the sheath which protects a hollow needle as indicated in the embodiments of FIGS. 1 to 5 or a conscious effort to employ a twist on the end of a blunt needle as in the embodiments of FIGS. 6 to 8. A conscious effort is also required with respect to the manually operated embodiments such as shown in FIGS. 9 and 10 in order to release the blunt protective needle. Once released, the sheath or blunt needle can be moved from the extended protective state to a retracted state to permit use of the hollow needle.

What is claimed is:

1. A protected needle assembly comprising
   a housing;
   a needle mounted on said housing;
   a sheath disposed concentrically about said needle with one end extending beyond said needle in protective relation, said sheath being movable longitudinally of said needle between an extended position covering over said needle and a retracted position exposing said needle;
   at least one projection on one of said sheath and said housing;
   locking means mounted on the other of said sheath and said housing for releasably locking said sheath in said extended position, said locking means including a guide slot receiving said projection, said guide slot having a circumferentially directed portion receiving said projection in said extended position of said sheath and a longitudinally directed portion receiving said projection during movement of said sheath to said retracted position; and
   resilient means for biasing said projection into said circumferentially directed portion of said guide slot.

2. A protected needle assembly as set forth in claim 1 wherein said locking means is a rigid sleeve mounted at one end on said housing and receiving said sheath therein in telescopic relation.

3. A protected needle assembly as set forth in claim 1 wherein said resilient means is a rubber sleeve secured to said housing at one end and secured to said sheath at an opposite end.

4. A protected needle assembly as set forth in claim 3 wherein said rubber sleeve has a wall at a distal end in facing relation to said needle for piercing thereby.

5. A protected needle assembly as set forth in claim 3 wherein said rubber sleeve and said sheath are coaxially disposed about said needle.

6. A protected needle assembly as set forth in claim 1 wherein said resilient means is a coiled spring disposed between said housing and said sheath.

7. A protected needle as set forth in claim 1 wherein said projection extends radially beyond said guide slot to permit manual operation thereof.

8. A protected needle assembly as set forth in claim 1 wherein said sheath is a rigid plastic tube.

9. A protected needle assembly as set forth in claim 8 wherein said tube is transparent to permit viewing of said needle.

10. A protected needle assembly comprising
    a housing;
    a hollow needle mounted on said housing;
    a blunt needle concentrically within said hollow needle for movement between an extended position with one end projecting out of said hollow needle and a retracted position with said end within said hollow needle;
    at least one projection on one of said blunt needle and said housing;
    locking means on the other of said blunt needle and said housing for releasably locking said blunt needle in said extended position, said locking means including a guide slot having a circumferentially directed portion receiving said projection in said extended position of said blunt needle and a longitudinally directed portion receiving said projection during movement of said blunt needle to said retracted position; and
    resilient means for biasing said projection into said circumferentially directed portion of said guide slot.

11. A protected needle assembly as set forth in claim 10 wherein said resilient means is a rubber sleeve secured between said blunt needle and said hollow needle.

12. A protected needle assembly as set forth in claim 10 which further comprises a vacuum holder needle extending coaxially of said blunt needle for effecting a blood transfer therebetween.

13. A protected needle assembly as set forth in claim 12 wherein said housing has a cup-shaped portion extending concentrically of said vacuum holder needle and a rubber sheath mounted on said housing and enclosing said vacuum holder needle.

14. A protected needle assembly as set forth in claim 10 wherein said blunt needle is solid.

15. A blood collecting assembly comprising a housing;

a blunt needle slidably mounted in said housing for movement between an extended position and a retracted position;

a hollow needle mounted concentrically about said blunt needle;

a sleeve rotatably mounted on said housing at one end thereof and secured to said hollow needle at an opposite end thereof, said sleeve having a guide slot therein including a pair of circumferentially directed portions and a longitudinally directed portion therebetween; and a projection secured to said blunt needle within said sleeve and received in said slot for movement from one of said circumferentially directed portions to secure said blunt needle in said extended position and projecting from said hollow needle into the other of said circumferentially directed portions to secure said blunt needle in said retracted position and disposed within said hollow needle.

16. A blood collecting assembly as set forth in claim 15 which further includes a resilient means for biasing said projection into a respective one of said circumferentially directed portions of said guide slot to maintain said blunt needle in one of said positions thereof.

17. A blood collecting assembly as set forth in claim 16 wherein said resilient means is a spring abutting said sleeve at one end and secured to said projection at an opposite end to permit resilient rotation of said sleeve relative to the projection.

18. A method for protecting a hollow needle, said method comprising the steps of disposing a sheath in telescopic relation relative to and outside a hollow needle having a sharp end for movement between an extended position projecting beyond said needle and a retracted position within the plane of said needle;

locking said sheath against longitudinal movement from said extended position to said retracted position;

rotating said sheath relative to said needle against a resilient force restoring means to unlock said sheath for movement from said extended position to said retracted position; and thereafter applying a longitudinally directed force on said sheath to move said sheath from said extended position to said retracted position and against said resilient force restoring means.

19. A method as set forth in claim 18 which further comprises the step of biasing said sheath back to said extended and locked position under the force imparted to said resilient means.

20. A method for protecting a hollow needle comprising the steps of disposing a blunt needle in telescopic relation within a hollow needle having a sharp end for movement between an extended position projecting beyond said needle and a retracted position within the plane of said needle;

locking said blunt needle against longitudinal movement from said extended position to said retracted position;

rotating said blunt needle relative to said hollow needle against a resilient force restoring means to unlock said blunt needle for movement from said extended position to said retracted position; and thereafter applying a longitudinally directed force on said blunt needle to move said blunt needle from said extended position to said retracted position and against said resilient force restoring means.

21. A protected needle assembly comprising a housing;

a needle mounted on said housing;

a sheath disposed concentrically about said needle with one end extending beyond said needle in protective relation; said sheath being movable longitudinally of said needle between an initial extended position covering over said needle and a retracted position exposing said needle;

at least one projection on said sheath;

locking means mounted on said housing for releasably locking said sheath in said extended position, said locking means including an L-shaped guide slot receiving said projection on said sheath, said guide slot having a circumferentially directed portion at a forward end receiving said projection in said extended position of said sheath and a longitudinally directed portion receiving said projection during movement of said sheath to and from said retracted position; and resilient means for biasing said projection from said longitudinally directed portion into said circumferentially directed portion of said guide slot.

22. A protected needle assembly as set forth in claim 21 when said resilient means is a rubber sleeve secured to said housing at one end and secured to said sheath at an opposite end.

23. A protected needle assembly as set forth in claims 22 wherein said rubber sleeve has a wall at a distal end in facing relation to said needle for piercing thereby.

24. A method for protecting a hollow needle, said method comprising the steps of disposing a sheath in telescopic relation relative to and outside a hollow needle having a sharp end for movement between an extended position projecting beyond said needle and a retracted position within the plane of said needle;

locking said sheath against longitudinal movement from said extended position to said retracted position;

abutting said sheath against one of a individual's skin, septum and a closure and rotating said sheath relative to said needle against a resilient force restoring means to unlock said sheath for movement from said extended position to said retracted position to permit penetration of said needle into said one of said skin, septum and closure; and thereafter applying a longitudinally directed force on said sheath to move said sheath from said extended position to said retracted position and against said resilient force restoring means while moving said needle into said one of said skin, septum and closure.

25. A protected needle assembly comprising a housing;

a needle mounted on said housing for percutaneous insertion into a patient;

a sheath disposed concentrically about said needle with one end extending beyond said needle in protective relation, said sheath being movable longitudinally of said needle between an extended position covering over said needle and a retracted position exposing said needle;

at least one projection on one of said sheath and housing;

locking means mounted on the other of said sheath and said housing for releasably locking said sheath in said extended position, said locking means including a guide slot receiving said projection, said guide slot having a circumferentially directed portion receiving said projection in said extended position of said sheath and a longitudinally directed portion receiving said projection during movement of said sheath to and from said retracted position; and resilient means for biasing said projection into said circumferentially directed portion of said guide slot.

26. A protected needle assembly as set forth in claim 25 wherein said locking means is a rigid sleeve mounted on one end of said housing and receiving said sheath therein in telescopic relation.

27. A protected needle assembly comprising a housing;

a needle mounted on said housing;

a sheath disposed concentrically about said needle with one end extending beyond said needle in protective relation, said sheath being movable longitudinally of said needle between an extended position covering over said needle and a retracted position exposing said needle;

at least one projection on said sheath;

a rigid tube mounted on said housing and over said needle, said tube including a guide slot receiving said projection on said sheath, said guide slot having a circumferentially directed portion receiving said projection in said extended position of said sheath and a longitudinally directed portion receiving said projection during movement of said sheath to said retracted position; and resilient means for biasing said projection into said circumferentially directed portion of said guide slot from said longitudinally directed portion.

* * * * *